(12) United States Patent
Leamy et al.

(10) Patent No.: US 6,711,952 B2
(45) Date of Patent: Mar. 30, 2004

(54) METHOD AND SYSTEM FOR MONITORING BEARINGS

(75) Inventors: Kevin Richard Leamy, Loveland, OH (US); Thomas Ulmont Watson, Hamilton, OH (US); William Joseph Simpson, Mason, OH (US); William Joseph Myers, Jr., West Chester, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/971,524

(22) Filed: Oct. 5, 2001

(65) Prior Publication Data

US 2003/0066352 A1 Apr. 10, 2003

(51) Int. Cl.$^7$ .............................................. G01N 29/00
(52) U.S. Cl. ........................... 73/579; 73/659; 73/660
(58) Field of Search .......................... 73/579, 659, 660, 73/593, 584, 662, 602, 600, 599; 702/39, 56, 35; 340/282, 283

(56) References Cited

U.S. PATENT DOCUMENTS

| | | | |
|---|---|---|---|
| 4,302,813 A | 11/1981 | Kurihara et al. | |
| 4,318,179 A | 3/1982 | Kure-Jensen et al. | 364/506 |
| 4,352,293 A | 10/1982 | Kurihara et al. | |
| 4,448,240 A | 5/1984 | Sharon | 364/508 |
| 4,453,407 A | 6/1984 | Sato et al. | 73/462 |
| 5,109,700 A | 5/1992 | Hicho | 73/660 |
| 5,115,671 A | 5/1992 | Hicho | 73/488 |
| 5,210,704 A | 5/1993 | Husseiny | 364/551.01 |
| 5,471,880 A | 12/1995 | Lang et al. | |
| 5,477,730 A | 12/1995 | Carter | 73/609 |
| 5,511,422 A | 4/1996 | Hernandez | 73/593 |
| 5,610,339 A | 3/1997 | Haseley et al. | 73/660 |
| 5,698,788 A | 12/1997 | Mol et al. | |
| 5,735,666 A | 4/1998 | Johnston | 415/35 |
| 5,749,660 A | 5/1998 | Dusserre-Telmon et al. | 384/475 |
| 5,804,726 A | 9/1998 | Geib et al. | 73/593 |
| 5,852,793 A | 12/1998 | Board et al. | 702/56 |
| 5,895,857 A * | 4/1999 | Robinson et al. | 73/602 |
| 6,014,598 A | 1/2000 | Duyar et al. | 701/29 |
| 6,053,047 A | 4/2000 | Dister et al. | 73/593 |
| 6,116,089 A * | 9/2000 | El-Ibiary et al. | 73/593 |
| 6,289,735 B1 * | 9/2001 | Dister et al. | 73/579 |
| 6,297,742 B1 * | 10/2001 | Canada et al. | 318/490 |
| 6,321,602 B1 * | 11/2001 | Ben-Romdhane | 340/679 |
| 6,510,397 B1 * | 1/2003 | Choe | 702/116 |

FOREIGN PATENT DOCUMENTS

| | | |
|---|---|---|
| DE | 3703946 | 8/1988 |
| EP | 0718608 | 6/1996 |

OTHER PUBLICATIONS

Dyer et al, "Detection of Rolling Element Bearing Damage by Statistical Vibration Analysis," *Trans. ASMe, 100* (Apr. 1978), pp. 229–235.

Jones, "Vibrations Help Find Faulty Components," *Machine Design*, (Feb. 25, 1999), pp. 85–88.

Braun et al, "Analysis of Roller–Ball Bearing Vibrations," *Trans. ASME, 101* (Jan. 1979), pp. 118–125.

(List continued on next page.)

Primary Examiner—Hezron Williams
Assistant Examiner—Jacques Saint-Surin
(74) Attorney, Agent, or Firm—W. Scott Andes; Hasse Guttag & Nesbitt LLC; Eric W. Guttag

(57) ABSTRACT

A method and system for monitoring the condition of a bearing mounted on a rotating shaft, particularly one present in an aircraft gas turbine engine, where the vibration sensor that monitors the bearing is remote therefrom but proximate to the rotating shaft. The vibration sensor obtains a broadband signal having frequencies that include the bearing defect peak of the monitored bearing. The broadband signal is analyzed to identify the presence of the bearing defect peak. If the bearing defect peak is present, the amplitude of this peak is quantified to determine whether degradation of the monitored bearing has at least reached a threshold criteria previously established.

22 Claims, 3 Drawing Sheets

OTHER PUBLICATIONS

Mathew et al, "The Condition Monitoring of Rolling Element Bearings Using Vibration Analysis," *Trans. ASME, 106* (Jul. 1984), pp. 447–453.

Berry, "How to Track Rolling Element Bearing Health with Vibration Signature Analysis," *Sound and Vibration*, (Nov. 1991), pp. 24–35.

Mori et al, "Prediction of Spalling on a Ball Bearing by Applying the Discrete Wavelet Transform to Vibration Signals," *Wear, 195* (1996), pp. 162–168.

Li et al., "On–Line Detection of Localized Defects in Bearings by Pattern Recognition Analysis," *Trans. ASME, 111* (Nov. 1989), pp. 331–336.

Li et al, "Acoustic Emission Analysis for Bearing Conditon Monitoring,"*Wear, 185* (1995), pp. 67–74.

Chaturvedi et al, "Bearing Fault Detection Using Adaptive Noise Cancelling," *Trans. ASME, 104* (Apr. 1982), pp. 280–289.

Ehrich, "Sum and Difference Frequencies in Vibration of High Speed Rotating Machinery," *Trans. ASME*, (Feb. 1972), pp. 181–184.

Schlitz, "Forcing Frequency Identification of Rolling Element Bearings," *Sound and Vibration*, (May 1990), pp. 16–19.

McFadden et al, "Vibration Monitoring of Rolling Element Bearings by the High–Frequency Resonance Technique–a Review," *Tribology*, 17(1) (Feb. 1984), pp. 3–10.

Ladd et al, "Proportional Bandwidth Properties of Fault Indicating Tones in a Ball Bearing System," *IEEE*, (1995), pp. 45–49.

Barkov et al, "Condition Assessment and Life Prediction of Rolling Element Bearings–Part 1" http://www.inteltek.com/articles/sv95/part1, pp. 1–22.

Barkov et al, "Condition Assessment and Life Prediction of Rolling Element Bearings–Part 1 2," http://www.inteltek.com/articles/sv95/part2, pp. 1–12.

Zoladz et al, "Bearing Defect Signature Analysis Using Advanced Nonlinear Signal Analysis in a Controlled Environment," *NASA Technical Memorandum 108491*, (May 1995), 1–39.

Fuller et al, "Bearing Detection in the Presence of Two Sources of Varying Coherence Using the Complex Cepstrum," *NASA Contractor Report 181605*, (Oct. 1987), pp. 1–33.

Li et al, "Bearing Localized Defect Detection Through Wavelet Decomposition of Vibrations," *Trans. ASME, 55* (1992), pp. 187–1962.

Li et al, "Acoustic Emission Analysis for Bearing Condition Monitoring," pp. 249–257.

Smith, "Vibration Monitoring of Bearings at Low Speeds," *Tribology*, (Jun. 1982), pp. 139–144.

Hite, "Real–Time Vibration Health Monitoring for Transiently Operating High–Speed Turbomachinery," pp. 359–372.

* cited by examiner

METHOD AND SYSTEM FOR MONITORING BEARINGS

BACKGROUND OF THE INVENTION

The present invention generally relates to a method and system for monitoring the condition of bearings mounted on a rotating shaft where the monitoring sensor is positioned remotely from the bearings. The present invention particularly relates to a method and system for remotely monitoring the condition of differential bearings mounted on rotating shaft in an aircraft gas turbine engine for the purpose of detecting defects therein prior to the point of bearing failure.

Rolling element bearings are used to facilitate rotation of a shaft relative to a stationary or rotating support, with minimal friction. They are typically comprised of concentric inner and outer races between which are positioned rolling elements. The rolling element can be a spherical ball (in the case of ball bearings) or a cylindrical roller element (in the case of roller bearings). Ball bearings are capable of supporting both radial and axial shaft loads, while roller bearings support radial loads only. The primary shaft race rotates synchronously with the shaft. In static housing bearings, the second race does not rotate and is supported by a stationary housing. In the case of intershaft or differential bearings, the second race rotates synchronously with a secondary shaft. Utilization of differential bearings can result in the advantages of significantly reduced system size and weight.

Like any other mechanical part, bearings can fail due to wear, lack of lubrication, contamination, assembly damage, excessive load or other factors. As a result, the monitoring of the condition of bearings has received considerable attention for some time because bearing failures can be catastrophic, leading to significant collateral damage and expensive repair, in addition to the time the machine is out of service. Monitoring of bearings to determine when they have or are about to become faulty can be more difficult when multiple bearing assemblies are being used in the machine, which is typical in gas turbine engines. Monitoring of bearing condition can be further complicated by other factors in the machine, such as high temperatures, difficulties in locating the monitoring sensors in the machine, other sources of vibration, and the like. When used with aircraft engines, the monitoring system also needs to be relatively lightweight.

An example of a gas turbine engine having multiple bearing assemblies is shown in U.S. Pat. No. 5,749,660 (Dusserre-Telmon et al), issued May 12, 1998. The turbine engine shown in FIG. 1 of the Dusserre-Telmon et al patent has six bearing assemblies (5 through 10) associated with a rotating shaft having a coaxial front part 1 and a rear part 2. These bearing assemblies include the combination of a ball bearing 5 and roller bearing 6 that support front part 1 of the shaft at the forward end of the engine, a pair of ball bearings 7 and 8 that support one end of the rear part 2 of the shaft and a pair of roller bearings 9 and 10 at the aft portion of the engine that support the other end of the rear part of 2 of the shaft.

In FIG. 1 of the Dusserre-Telmon et al patent, roller bearing 9 is shown in the form of an intershaft or differential roller bearing where both the inner and outer races are rotating. It has been found that for some aircraft engine models, intershaft bearing failures, i.e., at the position of roller bearing 9, can lead to aircraft engine in-flight shutdowns. A common failure mode for rolling element bearings of this type is localized defects, in which a sizable piece of the contact surface is dislodged during operation, mostly by fatigue cracking in the bearing metal under cyclic contact stressing. The monitoring of potential failure of such roller element bearings is thus often based on the detection of the onset of such localized defects.

One method for monitoring for such localized defects is to examine the debris present in the lubricant used in the bearing. Gas turbine engines typically have metal chip detectors (MCD) installed in the engine oil scavenge system. The MCD's collect metal debris that is transported in the lubricating oil; this collected metal debris can then be examined to determine if bearing material is present. Unfortunately, debris analysis can be unreliable for detecting defects in intershaft bearings because the bearing debris can be trapped inside the rotor by centrifugal forces and thus remain undetected by an MCD.

Another method for monitoring such localized defects is by vibration analysis. During bearing operation, bursts of acoustic emissions or vibrations result from the passage of the defect through the roller and raceway contacts. Defects at different locations of a bearing (inner race, roller and outer race) will have characteristic frequencies at which the bursts are generated. Theoretical estimations of these frequencies are called characteristic defect frequencies. Therefore, the signal of a damaged bearing (hereafter referred to as the "bearing defect peak") will typically consist of a periodic burst of acoustic emissions or vibrations near or about the characteristic defect frequency. In addition, the changing amplitude of this bearing defect peak over time can be used to quantify the degree of bearing failure that has occurred, preferably sufficiently in advance so that maintenance and repair can occur before there is total bearing failure. Unfortunately, the characteristic frequencies are usually sufficiently high that they can attenuate rapidly in the surrounding structures. For this reason, it is generally desirable to locate vibration sensors as close to the bearing as possible.

A particular problem in gas turbine engines exists when an intershaft or differential bearing, like bearing 9 in the Dusserre-Telmon et al patent, is positioned in a high temperature section of the engine. This makes it extremely difficult or potentially impossible to position a reliable vibration sensor close to this bearing so that it will survive and function in a high temperature environment. As a result, in the high temperature sections of the engine, the nearest practical location where sensors can survive and function are on the exterior of the engine. However, due to their high frequencies, characteristic bearing defect signals are usually attenuated before they can reach external engine sensor locations, meaning the defect will typically remain undetected.

Isolating the characteristic bearing defect frequency and amplitude from other acoustic emissions can also be difficult. Usually, the vibration sensor signal contains broadband frequency content (i.e., numerous frequencies across a broad frequency range); within this content is the characteristic bearing defect frequency which co-mingles with these other frequencies. The bearing defect peak at the characteristic frequency also does not necessarily have the highest amplitude, and is not typically self-evident. In addition, other sources of vibration can reside at the same frequency as the characteristic bearing defect frequency, which could lead to false detection events. For example, the signal can potentially be an aberration due to fluctuations in the rotational speed of the shaft, as well as the inner and outer races.

Accordingly, it would be desirable to provide a method and system for remotely monitoring the condition of bearings mounted on a rotating shaft, especially one used in a gas turbine engine, where multiple bearing assemblies are present, that can reliably detect and isolate the signal of the characteristic frequency of bearing failure of interest from a broadband signal, without invasive analysis techniques, and is relatively lightweight for use with aircraft engines.

SUMMARY OF THE INVENTION

The present invention relates to a method and system for monitoring the condition of a bearing mounted on a rotating shaft, particularly one present in a gas turbine engine of an aircraft, where the vibration sensor that monitors the bearing is remote therefrom but proximate to the rotating shaft. The method of the present invention comprises the steps of and the system of the present invention is capable of:

a. obtaining through the vibration sensor a broadband signal having frequencies that include the bearing defect peak of the monitored bearing;

b. analyzing the broadband signal to identify the presence of the bearing defect peak; and c. if the bearing defect peak is present, quantifying the amplitude of this peak to determine whether degradation of the monitored bearing has at least reached a threshold criteria previously established.

The method and system of the present invention provides a number of benefits and advantages in monitoring bearings mounted on a rotating shaft, especially one used in an aircraft gas turbine engine. The method and system of the present invention allows for reliable detection, isolation, identification and quantification of the bearing failure signal for the bearing of interest that is being monitored, even when multiple bearing assemblies are mounted on the rotating shaft. The method and system of the present invention provides a non-invasive analytical technique so that the bearing being monitored does not have to be removed to carry out the analysis. Because the vibration sensor can be mounted in the forward, lower temperature end of a gas turbine engine, the method and system is particularly useful in monitoring intershaft or differential bearings mounted at the aft, higher temperature end, of the gas turbine engine. The system of the present invention is also relatively lightweight, making it ideal for monitoring bearings in aircraft gas turbine engines.

The method and system of the present invention takes advantage of an alternate, less obvious transmission path for monitoring the condition of bearings mounted on a rotating shaft, especially one used in an aircraft gas turbine engine. It has been found that when the vibration sensor can be practically located proximate or near the shaft, with a relatively low mass between the sensor and the bearing being monitored, the characteristic defect frequency can be detected, even when the sensor is relatively remote from the bearing being monitored. In particular, the vibration sensor can be located in a lower temperature section of a gas turbine engine, yet detect a defect in a bearing located remotely therefrom in the higher temperature section of the engine when: (1) the vibration sensor is positioned proximate to the shaft; and (2) the portion of the shaft between the sensor and the bearing being monitored is of relatively low mass so that acoustic vibrations from the bearing will be transmitted by the shaft and picked up by the sensor.

BRIEF DESCRIPTION OF THE DRAWINGS

FIG. 1 is a side sectional view of a gas turbine engine that the method and system of the present invention can be used in.

DETAILED DESCRIPTION OF THE INVENTION

As used herein, the term "bearing defect peak" refers to the peak in the signal obtained for the bearing being monitored that is indicative of a bearing defect that can be identified and quantified to determine the degree of bearing failure or degradation over time.

As used herein, the terms "transmit" and "transmission" refers to any type of transmission that can be carried out electronically by wired methods, wireless methods or combinations thereof. Typical electronic transmissions within the scope of the present invention can be carried out by a variety of remote electronic transmission methods, such as by using Local or Wide Area Network (LAN or WAN)-based, Internet-based, or web-based transmission methods, cable television or wireless telecommunications networks, or any other suitable remote transmission method.

As used herein, the term "software" refers to any form of programmed machine-readable language or instructions (e.g., object code) that, when loaded or otherwise installed, provides operating instructions to a machine capable of reading those instructions, such as a computer or other computer program reader. Software useful in the present invention can be stored or reside on, as well as be loaded or installed from, one or more floppy disks, CD ROM disks, hard disks or any other form of suitable non-volatile electronic storage media. Software useful in the present invention can also be installed by downloading or other form of remote transmission.

As used herein, the term "comprising" means various components, capabilities and/or steps can be conjointly employed in the present invention. Accordingly, the term "comprising" encompasses the more restrictive terms "consisting essentially of" and "consisting of".

Figure 1:
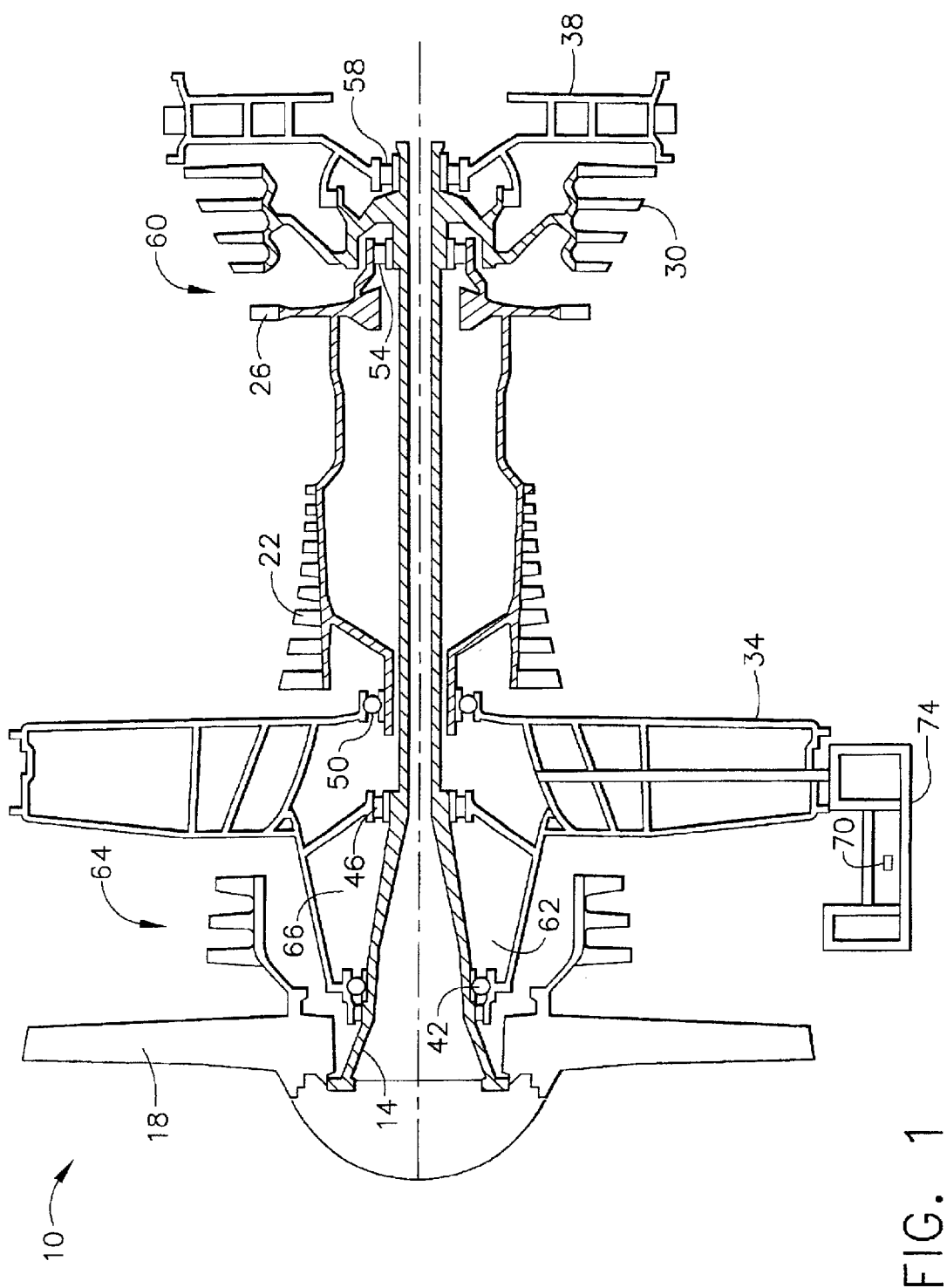

Referring to FIG. 1, a gas turbine engine for which the method and system of the present invention is useful is indicated generally as 10. While particularly useful in monitoring bearings mounted on rotating shafts in aircraft gas turbine engines, the method and system of the present invention can also be used to monitor bearings mounted on rotating shafts used with other machines such as steam turbine engines, helicopter gearboxes, gas turbine electrical generators, pumps, electrical motors, reciprocating engines, etc., where the vibration sensor is located remotely from the bearing being monitored but proximate to the rotating shaft.

Engine 10 is shown as having two rotors and five bearings with two frames for rotor support, i.e., an engine with multiple bearing assemblies. Engine 10 includes a rotating low pressure (LP) shaft 14 that extends along a longitudinal axis from the forward end to the aft end of the engine. As shown in FIG. 1, a fan rotor 18 is located at the forward end of engine 10, while a low pressure turbine (LPT) rotor 30 is located at the aft end of engine 10. The fan rotor 18 and the LPT rotor 30 together comprise the LP rotor assembly of engine 10 and are connected by LP shaft 14.

Engine 10 further includes a high pressure compressor (HPC) rotor 22 located aft of fan rotor 18 and a high pressure turbine (HPT) rotor 26 located forward of LPT rotor 30. The HPC rotor 22 is connected directly to the HPT rotor 26 and together comprise the high pressure (HP) rotor assembly of engine 10. The LP shaft 14 and the HP rotor assembly (i.e., HPC rotor 22 and HPT rotor 26) are concentric, with the LP shaft 14 being positioned to rotate within the HP rotor assembly.

As shown in FIG. 1, the LP rotor assembly (i.e., fan rotor 18, LPT rotor 30 and LP shaft 14) and the HP rotor assembly (i.e., HPC rotor 22 and HPT rotor 26) are supported or mounted using multiple bearing assemblies, five of which are indicated generally as 42, 46, 50, 54 and 58. The first and third bearing assemblies 42 and 50 are ball bearings, while the second, fourth and fifth bearing assemblies 46, 54 and 58 are roller bearings. Each rotor assembly requires a ball bearing for axial support, with the remainder of the support being provided by the roller bearings. The LP rotor assembly is supported by ball bearing 42 and roller bearing 46 at the forward end, and by roller bearing 58 at the aft end. The HP rotor assembly is supported by ball bearing 50 at the forward end and roller bearing 54 at the aft end. Bearings 42, 46 and 50 are static housing bearings supported by forward frame 34, while bearing 58 is a static housing bearing that is supported by rear frame 38.

Bearing 54 is an intershaft or differential bearing that is typically of the roller bearing type with both inner and outer races rotating. Bearing 54 supports the aft end of the HP rotor assembly (i.e., HPC rotor 22 and HPT rotor 26) on LP rotor shaft 14. The use of an intershaft bearing at the location of bearing 54 eliminates the need for another frame (in addition to frames 34 and 38) and thus significantly reduces engine size and weight.

Because of its location in the LPT section 60 of engine 10, differential roller bearing 54 is difficult to monitor directly to determine when the bearing has become sufficiently degraded and faulty to require maintenance or repair. This is due primarily to the higher temperatures that occur in the LPT section of engine 10 that can adversely affect vibration sensors located therein. As a result, the vibration sensor that monitors differential roller bearing 54 is located remotely therefrom so as to be in the lower temperature section 64 of engine 10. As shown in FIG. 1, the vibration sensor in the form of accelerometer 62 is located at the forward end of engine 10 near bearing assembly 42 and proximate to shaft 14. Because accelerometer 62 is proximate to shaft 14, it can obtain acoustic emissions or vibrations emanating from remotely located differential roller bearing 54 that are transmitted (via shaft 14) due to the relatively low rotor mass between accelerometer 62 and bearing 54. The positioning of accelerometer 62 proximate to forward frame 34 also allows transmission wires to be conveniently led out to an engine vibration monitor (not shown).

In determining whether bearing failure is occurring in differential roller bearing 54, the speed of rotation of the inner and outer races needs to be determined. A first speed sensor indicated as 66 that is located near the second bearing assembly 46 is used to monitor the speed of rotation of the inner (LP) race of differential roller bearing 54. A second speed sensor indicated as 70 that is located in gearbox 74 is used to monitor the speed of rotation of the outer (HP) race of differential roller bearing 54.

Figure 2:
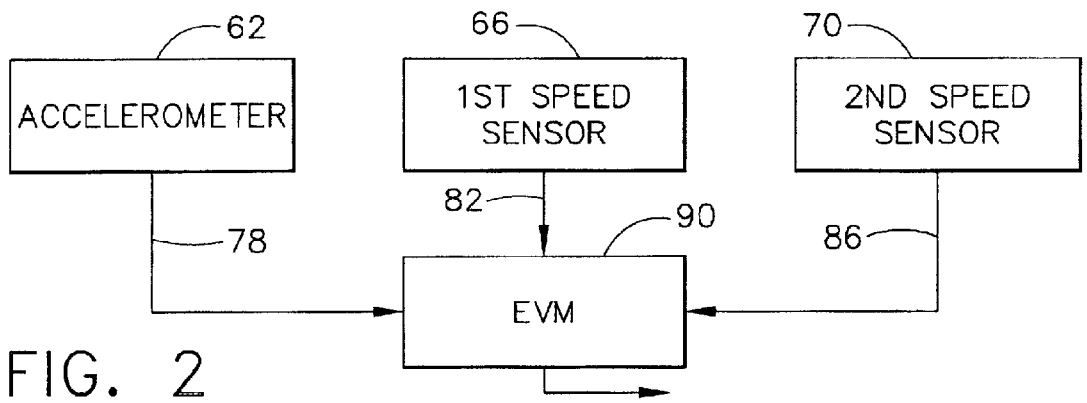
FIG. 2 is a schematic vibration and speed signal collecting and processing component that can be used in the method and system of the present invention.

As shown in the schematic in FIG. 2, accelerometer 62 provides a broadband signal indicated generally as 78 based on the acoustic emissions or vibrations collected, including those from differential roller bearing 54). The first speed sensor 66 obtains a signal 82 on the speed of rotation of the inner race of differential roller bearing 54, while the second speed sensor 70 obtains a signal 86 on the speed of rotation of the outer race of differential roller bearing 54. As shown in FIG. 2, signals 78, 82 and 86 are collected by an engine vibration monitor (EVM) 90 or similar monitoring unit located on the aircraft or engine 10 that typically includes processing capability (e.g., a digital signal processor), random access memory (RAM) and non-volatile storage capability (e.g., a hard disk), i.e., monitor 90 is typically computerized. As a result, monitor 90 usually has the capability to further process and analyze the collected signals 78, 82 and 86, as well as to store the results of such processing and analysis. Monitor 90 can also transmit the collected or processed signals to another remote system (e.g., while the aircraft is still in the air), or can simply store the collected or processed signals for later transmission or downloading to another system (e.g., after the aircraft has landed). For example, the collected or processed signals can be transmitted or downloaded to a computer (e.g., a portable computer).

Because signal 78 is a broadband signal (e.g., typically in the range from 0 to about 4000 Hz.), it is usually difficult or impossible to directly identify in signal 78 the relevant bearing defect peak for differential roller bearing assembly 54. Indeed, the peak with the highest amplitude in signal 78 is not always the one that is the bearing defect peak. Accordingly, the broadband signal 78 is typically filtered to narrow the bandwidth that covers the range of frequencies that include the bearing defect peak (e.g., typically in the range from about 2000 to about 3000 Hz.). This filtering to a narrower bandwidth usually allows for easier identification and quantification of the bearing defect peak. The ranges for these broadband and narrowband signals can vary (upwardly or downwardly) depending on several factors, such as the number of rolling elements in the bearings, the relative rotor speeds, and the degree of bearing slip (i.e., when the tangential velocity of the rolling element does not match the tangential velocity of the race).

In addition, knowledge of the speed of the LP and HP races provided by signals 82 and 86, respectively, which is also indicative of the engine shaft speeds, is needed to insure that signals 78 collected at different times are comparable. Signals 78 can be collected during a period of time when engine speeds are changing (referred to hereafter as "transient" engine speed conditions) or when engine speeds are constant or stable (referred to hereafter as "steady state" engine speed conditions). Analysis of signals 78 collected under both "transient" and "steady state" conditions can be useful in detecting the potential failure of differential roller bearing 54. Detection of potential failure of differential roller bearing 54 also typically requires the collection and analysis of many signals 78 over a period of time. This ensures that the detection of bearing failure is based on repetitive objective determinations of a sufficient sample of the collected data, and not a potentially aberrant phenomena.

Figure 3:
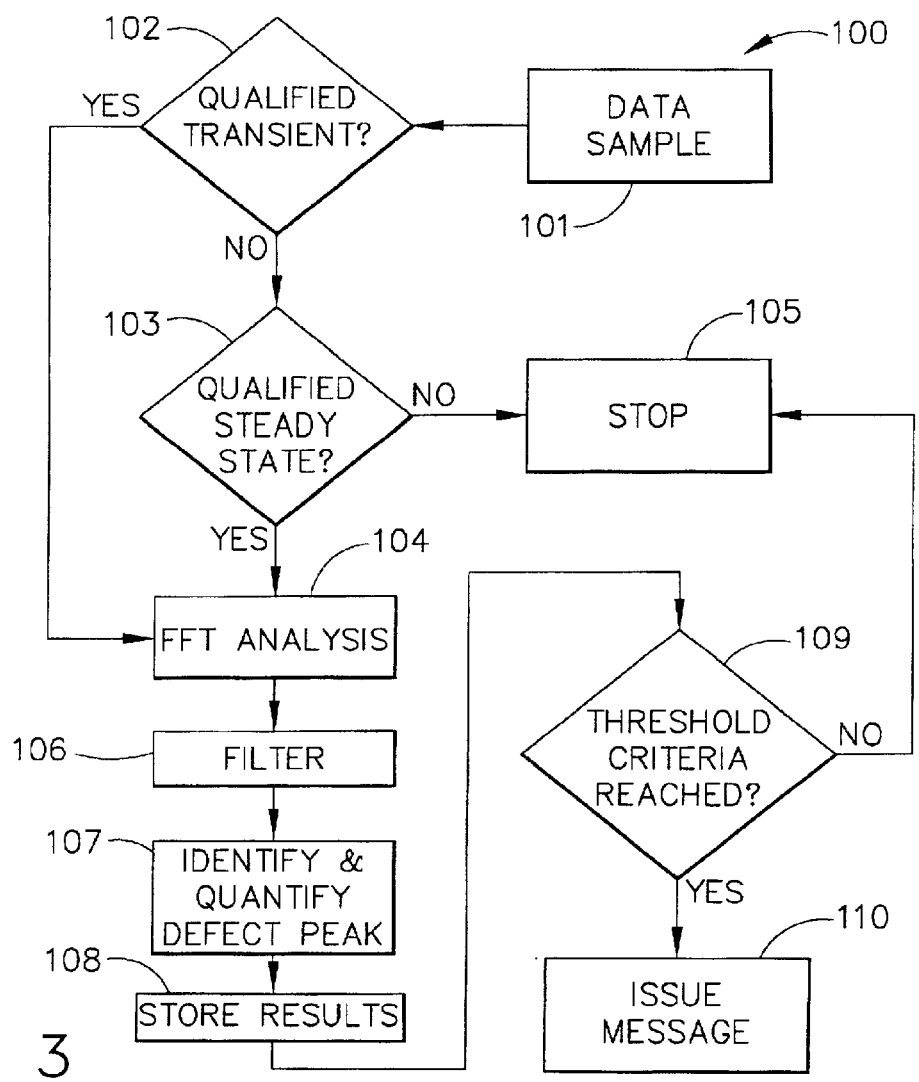
FIG. 3 represents a flowchart illustrating the steps that can be carried out according to an embodiment of the method and system of the present invention.

An embodiment of the method of the present invention is illustrated by the flowchart generally indicated as 100 in FIG. 3. Referring to FIG. 3, in step 101, a data sample is obtained by monitor 90 that contains collected signals, 78, 82 and 86. As indicated by step 102, an initial query is performed to qualify whether the data sample was obtained under appropriate transient conditions. If the data sample was not obtained under appropriate transient conditions (the answer to "Qualified Transient?" in step 102 is "No"), another query is performed as indicated by step 103 as to whether the data sample was obtained under appropriate steady state conditions. If the data sample was obtained under appropriate transient conditions (the answer to "Qualified Transient?" in step 102 is "Yes"), the data sample is then processed further per step 104. If the data sample was not obtained under appropriate steady state conditions (the answer to "Qualified Steady State?" in step 103 is "No"), the data sample is not processed further since it would not provide reliable or comparable results, as indicated in step 105. If the data sample was obtained under appropriate steady state conditions (the answer to "Qualified Steady State?" in step 103 is "Yes"), the data sample is then processed further per step 104.

In step 104, the data sample is then analyzed using Fast Fourier Transformation (FFT) analysis techniques to obtain a spectrum or graphical display of the broadband signal 78. A broadband periodic signal typically includes contributions from many frequencies. The FFT analysis provides a spectrum of the individual frequencies present within a broadband signal, indicating the strength of each frequency's contribution. Typically, a normal FFT of a gas turbine engine will include predictable content, including integer and specific non-integer harmonics of frequencies which correspond to LP and HP rotor assembly speeds, and of fixed frequency phenomena. The characteristic defect frequency is generally predictable from the bearing geometry and the rotor speeds. However, the characteristic defect frequency can vary due to bearing slip and can also contain frequency sidebands which can be higher in amplitude than the primary characteristic defect frequency. For this reason, it usually becomes necessary to evaluate a characteristic defect frequency range which includes the characteristic defect frequency, as well as expected variations and possible sidebands. The portion of the FFT within the characteristic defect frequency range is then extracted for further evaluation.

Figure 4:
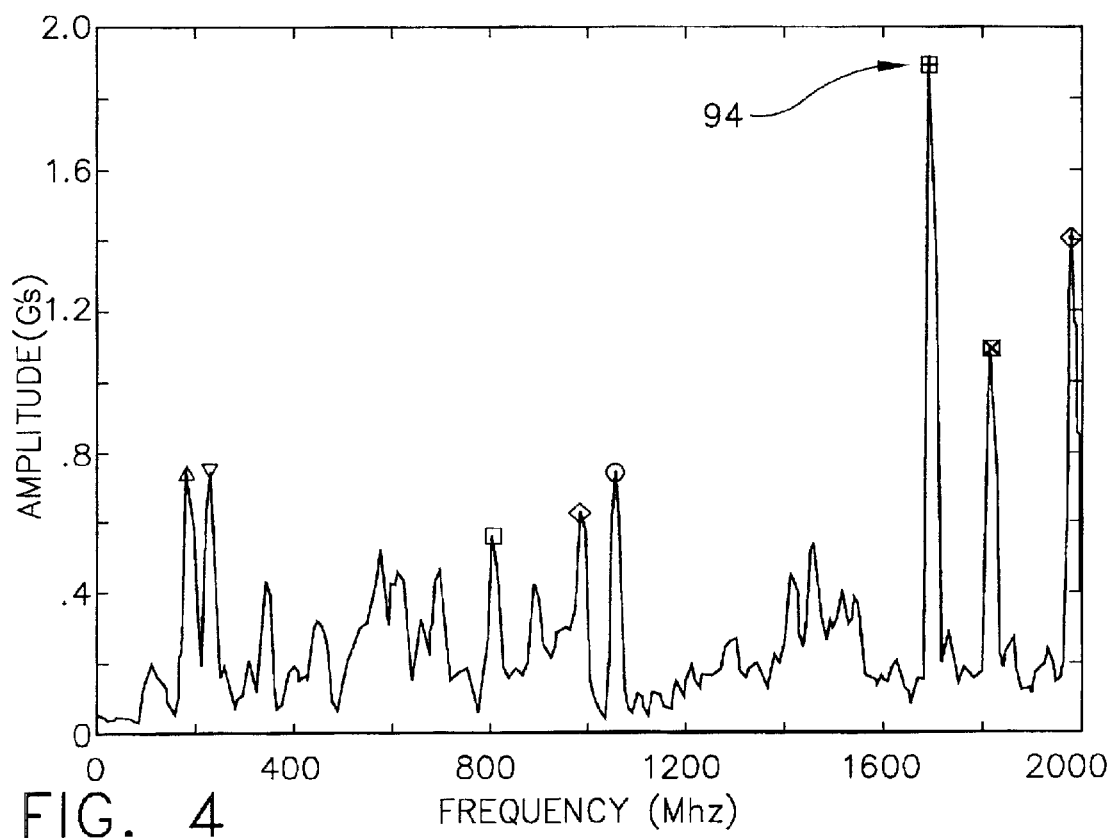
FIG. 4 is a representative graphical display broadband vibration signal obtained by the vibration sensor in the method and system of the present invention.

One such FFT graphical display is shown in FIG. 4 where the peak having the highest amplitude indicated by 94 happens to be the bearing defect peak. However, this is not always the case. In those instances where the bearing defect peak is lower in amplitude than other frequency components, it is typically necessary to isolate it from other frequencies. Accordingly, all of the predictable content not related to the bearing defect (including integer and specific non-integer harmonics of frequencies which correspond to LP and HP rotor assembly speeds, and of fixed frequency phenomena) are removed or filtered from the FFT in step 106 to provide a narrow bandwidth range of frequencies, including the frequency that includes the bearing defect peak.

After filtering out the known non-defect related frequencies, the amplitude and frequency of the highest remaining peak in the characteristic defect frequency range is measured in step 107. The amplitude is recorded as the bearing defect peak, and the frequency is recorded as the characteristic defect frequency. After quantification of the amplitude of the bearing defect peak, the results of such a quantification can be compiled or stored, as shown in step 108. As shown in step 109, a determination is then made as to whether the amplitude of this peak has reached or exceeded a threshold criteria previously established for a predetermined number of occasions, at consistent characteristic defect frequencies. (This typically requires repeated determinations showing that the threshold criteria has been consistently reached or exceeded.) If the threshold frequency criteria has been consistently reached or exceeded (the answer to "Threshold Criteria Reached" is "Yes"), a message (e.g., an alarm) is then issued per step 110 so that appropriate action (e.g., maintenance or repair of the bearing) can be taken. If the threshold frequency criteria has not been consistently reached or exceeded (the answer to "Threshold Criteria Reached" is "No"), the process again terminates per step 105. If desired, step 110 can be comprised of a multiple of steps for different levels of messages (e.g., alarms) to be issued, depending on the degree of the bearing degradation or failure shown by the height of the amplitude of the bearing defect peak.

Figure 5:
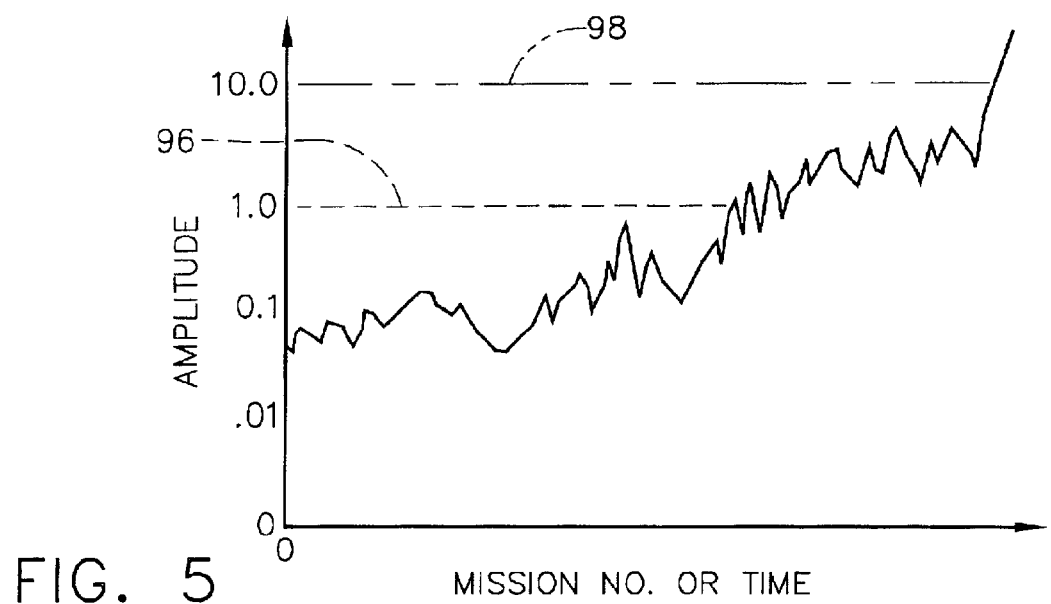
FIG. 5 is a representative graphical display of the amplitudes of the bearing defect peak value over time.

Usually many data samples are analyzed using the embodiment of the method illustrated in steps 101 through 110 to obtain a plot of the amplitude values of the bearing defect peak. One such graphical plot is shown in FIG. 5 which also includes various threshold criteria lines to indicate how serious the degree of the bearing degradation is and what and when appropriate action should be taken. For example, the line indicated by 96 represent a "caution" threshold (e.g., the monitored bearing could require maintenance or repair relatively soon), while the line indicated by 98 represents an "alert" threshold (e.g., the monitored bearing requires immediate maintenance or repair.) Indeed, by plotting these amplitude values over time, the bearing degradation trend can be progressively monitored to provide sufficient warning as to when to take appropriate corrective action.

The embodiment of the method illustrated in steps 101 through 110 can be carried out entirely by monitor 90, i.e., an automated computerized system for monitoring the condition of the bearing and determining when maintenance or repair thereof is advisable or immediately required. In such a computerized system, monitor 90 could be provided with a display to issue the message in step 110 as to whether the threshold criteria for taking a particular action has been reached or exceeded or could issue such a message as the collected or processed data is downloaded or transmitted to another system. Alternatively, monitor 90 could simply store the collected or processed data (i.e., as in step 108). This collected or processed data could then be subsequently downloaded or transmitted for further analysis to determine potential trends to predict when the threshold criteria are likely to be reached or exceeded (per step 109) and when maintenance or repair messages at one or more levels should be issued (per step 110).

The present invention can also be provided in the form of downloadable or otherwise installable software that can be installed on and utilized by a computerized monitor 90 to carry out the embodiment of the method described in steps 101 through 110. This software can be provided or associated with a set of instructions for downloading or installation of the software on monitor 90 and/or use of the software with monitor 90 that are written or printed on one or more sheets of paper, in a multi-page manual, at the location where the software is located for remote downloading or installation (e.g., a server-based web site), on or inside the packaging in which the software is provided or sold, and/or on the electronic media (e.g., floppy disk or CD ROM disk) from which the software is loaded or installed, or any other suitable method for providing instructions on how to load, install and/or use the software.

While specific embodiments of the method, system and software of the present invention have been described, it will be apparent to those skilled in the art that various modifications thereto can be made (including the order of the various steps) without departing from the spirit and scope of the present invention as defined in the appended claims.

What is claimed is:

1. A method for monitoring the condition of a bearing mounted at one end on a rotating shaft wherein a vibration sensor that monitors the bearing is mounted at the other end of the rotating shaft but proximate thereto, the method comprising the steps of:
   a. obtaining through the vibration sensor a broadband signal having frequencies that include the bearing defect peak of the monitored bearing;
   b. analyzing the broadband signal to identify the presence of the bearing defect peak; and
   c. if the bearing defect peak is present, quantifying the amplitude of the bearing defect peak to determine whether degradation of the monitored bearing has at least reached a threshold criteria previously established.

2. The method of claim 1 wherein the rotating shaft is present in an aircraft gas turbine engine.

3. The method of claim 2 wherein multiple bearings are mounted on the rotating shaft.

4. The method of claim 2 wherein the engine comprises a higher temperature section and lower temperature section, and wherein the bearing being monitored is located in the higher temperature section and the vibration sensor is located in the lower temperature section.

5. The method claim 2 wherein the bearing being monitored is a differential roller bearing having an inner rotating race and an outer rotating race and wherein the rotational speed of the inner race end the rotational speed of the outer race are obtained and included in the analysis of the broadband signal in step (b).

6. The method of claim 5 wherein the rotational speeds of the inner and outer races are obtained during transient engine speed conditions.

7. The method of claim 5 wherein the rotational speeds of the inner and outer races are obtained during steady state engine speed conditions.

8. The method of claim 2 which comprises the further step (d) of issuing a message as to the appropriate action to be taken if it is determined during step (c) that the threshold criteria has at least been reached.

9. The method of claim 2 wherein step (c) comprises obtaining a plot of the amplitude values of the bearing defect peak to progressively monitor the degradation of the bearing.

10. A system for monitoring die condition of a bearing mounted at one end on a rotating shaft, the system comprising:
   (a) a vibration sensor mounted at the other end of the rotating shaft but proximate thereto, the vibration sensor being capable of obtaining a broadband signal having frequencies that include a bearing defect peak of the monitored bearing; and
   (b) a vibration monitor that is capable of:
      (1) collecting the broadband signal from the vibration sensor;
      (2) analyzing the broadband signal to identify the presence of the bearing defect peak; and
      (3) if the bearing defect peak is present, quantifying the amplitude of the bearing defect peak to determine whether degradation of the monitored bearing has at least reached a threshold criteria previously established.

11. The system of claim 10 wherein the rotating shaft is present in an aircraft gas turbine engine.

12. The system of claim 11 wherein multiple bearings are mounted on the rotating shaft.

13. The system claim 12 wherein the engine comprises a higher temperature section and lower temperature section, and wherein the bearing being monitored is located in the higher temperature section and the vibration sensor is located in the lower temperature section.

14. The system of claim 13 wherein the bearing being monitored is a differential roller bearing having an inner rotating race and an outer rotating race and wherein the system further comprises a first speed sensor and a second speed sensor, the first speed sensor obtaining a signal on the rotational speed of the inner race and the second speed sensor obtaining a signal on the rotational speed of the outer race, and wherein the vibration monitor collects and includes the signals obtained by the first and second speed sensors in the analysis of the broadband signal in step (b).

15. The system of claim 14 wherein the vibration monitor is capable of issuing a message as to the appropriate action to be taken if it is determined during step (c) that the threshold criteria has at least been reached.

16. Software for use in a computerized system for monitoring the condition of a bearing mounted at one end on a rotating shaft, the system including a vibration sensor mounted at the other end of the rotating shaft but proximate thereto, the vibration sensor being capable of obtaining a broadband signal having frequencies that include a bearing defect peak of the monitored bearing and a vibration monitor capable of installing and utilizing the software: the software being capable, when installed on the vibration monitor, of:
   (a) collecting the broadband signal from the vibration sensor;
   (b) analyzing the broadband signal to identify the presence of the bearing defect peak; and
   (c) if the bearing defect peak is present, quantifying the amplitude of the bearing defect peak to determine whether degradation of the monitored bearing has at least reached a threshold criteria previously established.

17. The software of claim 16 that is stored and installable from one or more nonvolatile electronic storage media.

18. The software of claim 17 wherein the electronic media are floppy disks or CD ROM disks.

19. The software or claim 18 which has instructions provided or associated therewith for how to use the software with the system, how to install the software on the system, or how to use with and install the software on the system.

20. The software of claim 16 wherein the rotating shaft is present in an aircraft gas turbine engine.

21. The software of claim 20 wherein the bearing being monitored is a differential roller bearing having an inner rotating race and an outer rotating race and wherein the system further comprises a first speed sensor and a second speed sensor, the first speed sensor obtaining a signal on the rotational speed of the inner race and the second speed sensor obtaining a signal on the rotational speed of the outer race, and wherein the software is capable of allowing the vibration monitor to collect and include the signals obtained by the first and second speed sensors in the analysis of the broadband signal in step (b).

22. The software of claim 21 which is capable of allowing the vibration monitor to issue a message as to the appropriate action to be taken if it is determined during step (c) that the threshold criteria has at least been reached.

* * * * *

UNITED STATES PATENT AND TRADEMARK OFFICE
CERTIFICATE OF CORRECTION

PATENT NO.   : 6,711,952 B2
DATED        : March 30, 2004
INVENTOR(S)  : Kevin Richard Leamy et al.

It is certified that error appears in the above-identified patent and that said Letters Patent is hereby corrected as shown below:

Column 10,
Line 44, after the word "software", delete the word "or" and insert the word -- of --.

Signed and Sealed this

Thirty-first Day of May, 2005

JON W. DUDAS
*Director of the United States Patent and Trademark Office*